(12) United States Patent
Bae et al.

(10) Patent No.: US 7,297,248 B2
(45) Date of Patent: Nov. 20, 2007

(54) GLUCOSE STRIP SENSOR AND GLUCOSE MEASUREMENT METHOD USING THE GLUCOSE STRIP SENSOR

(75) Inventors: Byung-Woo Bae, Anyang-Si (KR); Byung-Soo Kang, Kwachon-Si (KR); Seong-Gi Park, Yongin-Si (KR); Seong-Dong Lee, Youngcheon-Si (KR); Mi-Joong Kwon, Seoul (KR)

(73) Assignee: Infopia Co., Ltd., Kyunggi-do (KR)

( * ) Notice: Subject to any disclaimer, the term of this patent is extended or adjusted under 35 U.S.C. 154(b) by 0 days.

(21) Appl. No.: 10/481,406

(22) PCT Filed: Oct. 10, 2001

(86) PCT No.: PCT/KR01/01702

§ 371 (c)(1),
(2), (4) Date: Dec. 30, 2003

(87) PCT Pub. No.: WO03/005015

PCT Pub. Date: Jan. 16, 2003

(65) Prior Publication Data

US 2004/0146958 A1    Jul. 29, 2004

(30) Foreign Application Priority Data

Jul. 7, 2001    (KR) ............................... 2001-40690

(51) Int. Cl.
*G01N 27/327* (2006.01)
(52) U.S. Cl. ............................... 205/777.5; 204/403.14
(58) Field of Classification Search ...............
204/403.01–403.03, 403.1–403.12, 403.14,
204/409, 412, 777.5, 779, 792, 793.5
See application file for complete search history.

(56) References Cited

U.S. PATENT DOCUMENTS 3,061,523 A    10/1962    Free ........................ 195/103.5

(Continued)

FOREIGN PATENT DOCUMENTS

JP    50-39558    4/1975

(Continued)

OTHER PUBLICATIONS

"Amperometric Glucose Microelectrodes Prepared through Immobilization of Glucose Oxidase in Redox Hydrogels," Anal. Chem. 1991, 63, 2268-2272.*

(Continued)

*Primary Examiner*—Alex Noguerola
(74) *Attorney, Agent, or Firm*—Greenblum & Bernstein, P.L.C.

(57) ABSTRACT

Disclosed is a disposable glucose strip sensor configured to rapidly and conveniently measure the concentration of glucose in blood and a glucose measurement method using the glucose strip sensor. In the glucose strip sensor, at least one checking electrodes are additionally provided at an electrode section including an operating electrode and a counter electrode. The checking electrode serves to check whether or not it is electrically connected with the counter electrode, upon measuring the concentration of glucose in a blood sample introduced in the sensor. Where two checking electrodes are provided, it may be checked whether or not an electrical connection is established between those checking electrodes. Based on the result of the checking, it is possible to determine whether or not a sufficient amount of blood sample is filled in the sensor. Accordingly, the measurement of glucose concentration can be accurately achieved.

11 Claims, 6 Drawing Sheets

U.S. PATENT DOCUMENTS

| | | | |
|---|---|---|---|
| 5,120,420 A | 6/1992 | Nankai et al. | 204/403 |
| 5,582,697 A * | 12/1996 | Ikeda et al. | 205/777.5 |
| 6,299,757 B1 * | 10/2001 | Feldman et al. | 205/775 |
| 6,436,256 B1 * | 8/2002 | Williams et al. | 204/403.06 |
| 6,458,258 B2 * | 10/2002 | Taniike et al. | 204/403.14 |
| 6,491,803 B1 * | 12/2002 | Shen et al. | 204/403.11 |
| 6,592,745 B1 * | 7/2003 | Feldman et al. | 205/777.5 |
| 6,793,802 B2 * | 9/2004 | Lee et al. | 205/777.5 |

FOREIGN PATENT DOCUMENTS

| | | |
|---|---|---|
| JP | 61-294351 | 12/1986 |
| KR | 85-1297 | 9/1985 |
| WO | 99/13099 | 3/1999 |
| WO | 99/13100 | 3/1999 |
| WO | 99/58709 | 11/1999 |
| WO | 00/73778 | 12/2000 |
| WO | 00/73785 | 12/2000 |
| WO | 00/79258 | 12/2000 |

OTHER PUBLICATIONS

English Language Abstract of korean 85-1297.
English Language Abstract of JP 61-294351.
English Language Abstract of JP 50-39558.

* cited by examiner

FIG. 1

- Prior Art-

FIG.2

- Prior Art -

GLUCOSE STRIP SENSOR AND GLUCOSE MEASUREMENT METHOD USING THE GLUCOSE STRIP SENSOR

BACKGROUND OF THE INVENTION

1. Field of the Invention

The present invention relates to a disposable glucose strip sensor configured to rapidly and conveniently measure the concentration of glucose in blood and a glucose measurement method using the glucose strip sensor.

2. Description of the Related Art

The measurement of the concentration of glucose in blood is of great importance not only to diabetic patients who must control their sugar intake, but also for the early detection and diagnosis of diabetes. To this end, methods for simply and conveniently measuring the concentration of glucose in blood have been proposed.

Known glucose measurement methods are based on oxidation of glucose by glucose-oxidase and peroxidase. They also use orthotolidine or a benzidine-based mixture as an indicator reagent, that is, a chromogen. In accordance with these methods, a color transition of the indicator reagent resulting from the oxidation of glucose is observed to measure the concentration of glucose in blood.

For example, such techniques are disclosed in U.S. Pat. No. 3,061,523 and Japanese Patent Publication No. Sho. 50-39558. In these references, a glucose-measuring test piece is disclosed. In order to prepare this test piece, a solution is prepared which has a composition including: glucose oxidase and peroxidase as enzymes; a citric acid buffer to maintain a pH of 6.0; gelatin, alginic acid, polyvinylpyrrolidone, and polyvinyl alcohol as stabilizers; and orthotolidine, benzidine, 3-aminopropylcarbarsone, and 2,7-diaminofluorene as a chromogen. The solution is impregnated into a cellulose paper which has a desired thickness and size to be used as a carrier, and then dried. Thus, the test piece is obtained. Also, Korean Patent Laid-open Publication No. 85-1297 discloses a method for manufacturing a glucose-measuring test piece, to which the basic principle of an enzymatic measurement method using glucose oxidase and peroxidase is applied. Where the concentration of glucose in blood is measured using the above mentioned glucose-measuring test pieces, it is difficult to accurately measure a glucose concentration because the measurement is based on a color transition exhibited on the test piece.

In order to solve the above mentioned problem, various techniques have been proposed which measure glucose concentration using an electrochemical method. Such an electrochemical method makes it possible to measure the concentration of glucose in blood with an increased accuracy while reducing measurement time and achieving convenience in measurement. By virtue of such advantages, the use of the electrochemical glucose measurement method has been greatly increased.

Now, the operating principle of a glucose-measuring sensor based on an electrochemical method will be described. When a blood sample is applied to a reaction layer of the glucose-measuring sensor, glucose contained in the blood sample is oxidized by a glucose-oxidizing enzyme contained in the reaction layer. At this time, the glucose-oxidizing enzyme is reduced. The reduced glucose-oxidizing enzyme is then oxidized by an electron acceptor, whereby the electron acceptor is reduced. The reduced electron acceptor donates electrons at the surface of an electrode to which a desired voltage is applied. As a result, the electron acceptor is electrochemically reoxidized. The concentration of glucose in the blood sample is proportional to the amount of current generated during the process in which the electron acceptor is oxidized. Accordingly, the concentration of glucose can be measured by measuring the amount of current.

Figure 1:
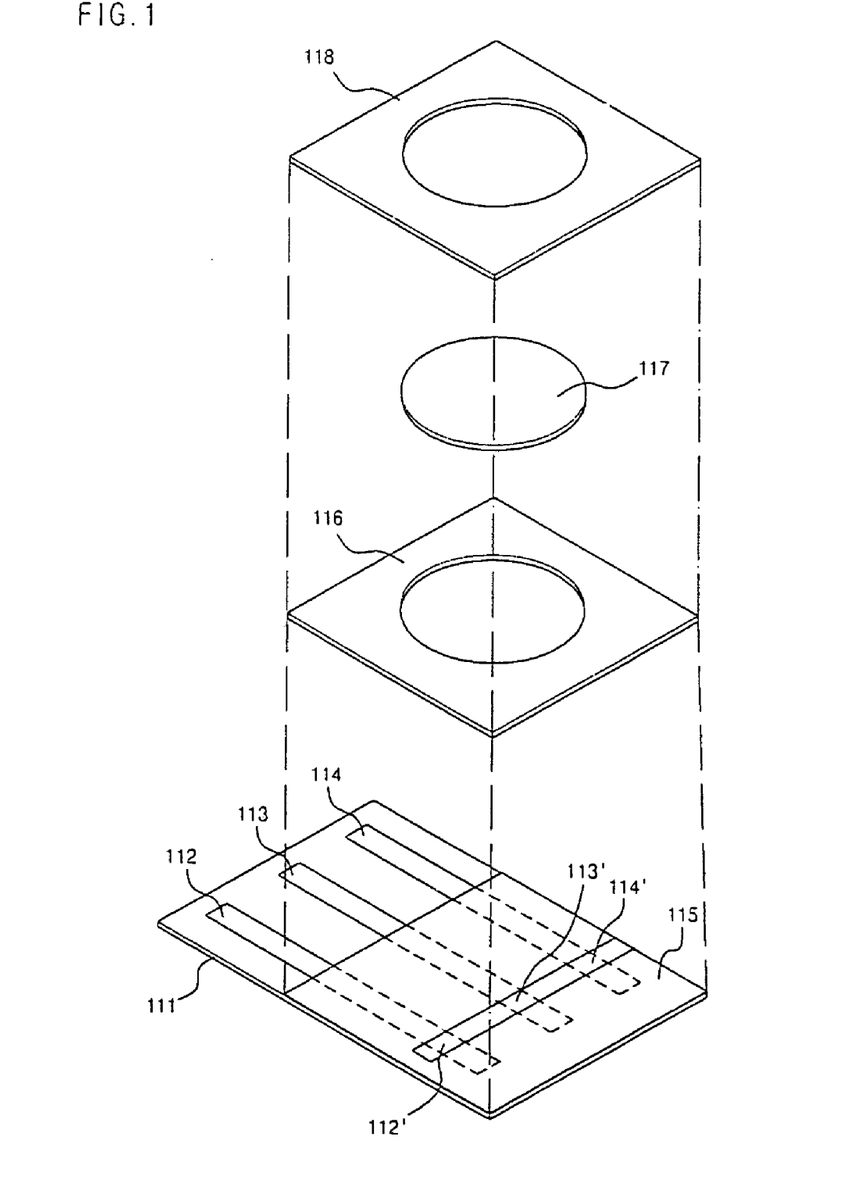
FIG. 1 is an exploded perspective view illustrating a conventional sample-dropped glucose-measuring test piece.

An example of the above mentioned glucose-measuring sensor is disclosed in Japanese Patent Laid-open Publication No. 61-294351. This sensor is illustrated in FIG. 1. As shown in FIG. 1, operating and counter electrodes, which are made of carbon or the like, are formed on a substrate 111 in a screen printing fashion. An insulator 115 is also formed on the substrate 111 while allowing the electrodes to be partially exposed. A porous reaction layer 117, which contains a reactive material such as a glucose-oxidizing enzyme and an electron acceptor, is arranged on the insulator 115. In order to firmly hold the porous reaction layer 117, a holding frame 116 and a cover 118 are arranged on the insulator 115. In FIG. 1, reference numerals 112, 113, and 114 denote the operating and counter electrodes, and reference numerals 112', 113', and 114' denote the exposed portions of the operating and counter electrodes. These electrodes and electrode portions form an electrode system. When a blood sample is dropped onto the porous reaction layer 117, the glucose-measuring sensor having the above mentioned structure can measure the concentration of glucose in the blood sample.

In this glucose-measuring sensor, however, the amount of blood absorbed in the reaction layer 117 varies depending on the amount of the blood sample dropped onto the reaction layer 117. As a result, measurement errors may be caused by a variation in the amount of blood absorbed in the reaction layer 117.

Figure 2:
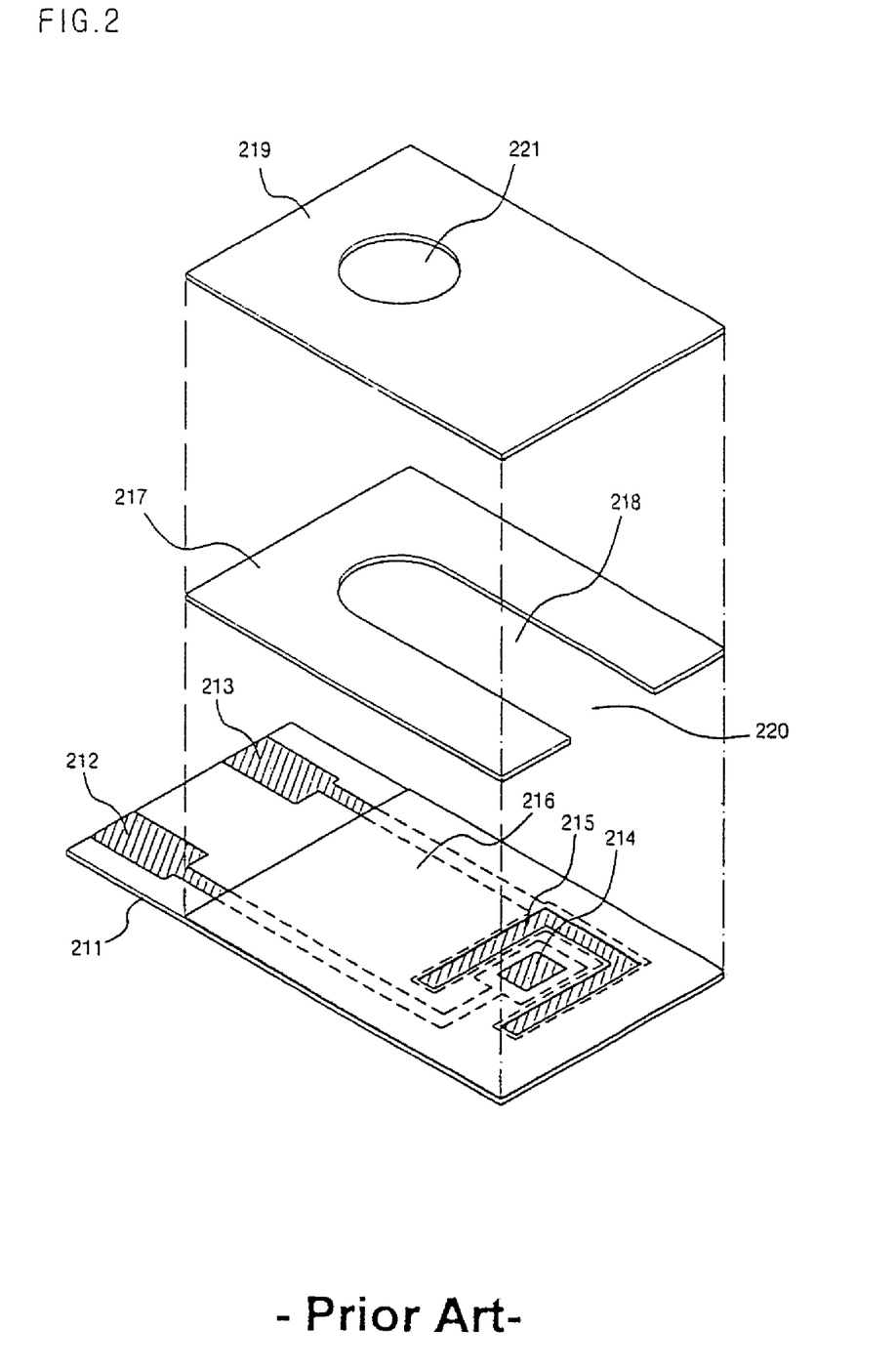
FIG. 2 is an exploded perspective view illustrating a conventional glucose-measuring biosensor utilizing capillary phenomenon.

In order to solve this problem, a biosensor has been proposed. An example of such a biosensor is disclosed in U.S. Pat. No. 5,120,420 and illustrated in FIG. 2. As shown in FIG. 2, this biosensor includes a non-conductive substrate 211 made of polyethylene terephthalate. Silver is screen-printed on the non-conductive substrate 211 to form leads 212 and 213. Conductive carbon paste containing a resin binder is printed on the leads 212 and 213, thereby forming an operating electrode 214 and a counter electrode 215. An insulator 216 is then printed to allow the electrodes 214 and 215 to be partially exposed. A 0.5% aqueous solution of carboxymethyl cellulose (CMC) is spread onto the electrodes 214 and 215, and dried to form a CMC layer. A solution of glucose oxidase (GOD) as the enzyme in a phosphate buffer solution is spread on the CMC layer, and dried to form a main reaction layer comprised of a CMC-GOD layer. Next, a resin plate 217 and a cover 219 are attached to the resulting structure while defining a space 218. In FIG. 2, the reference numeral 220 denotes a sample introducing port, and the reference numeral 221 denotes a discharge port.

In the biosensor having the above mentioned structure, when a sample solution comes into contact with the sample introducing port 220, it is introduced into the space 218 by virtue of capillary phenomenon, so that it fills the space 218. Simultaneously, air existing in the space 218 is vented from the space 218 through the discharge port 221 formed opposite to the sample introducing port 220 or at the cover 219.

Where the discharge port 221 is arranged at the upper surface of the biosensor, measurement errors may occur when the user unintentionally touches the discharge port 221. For this reason, there is inconvenience in handling the biosensor. Furthermore, the user can check whether or not a sufficient amount of sample solution is introduced in the biosensor, only with the naked eye. So, the measurement may be carried out even when an insufficient amount of sample solution is filled in the biosensor. In this case, however, the detected glucose level may erroneously be lower than the actual glucose concentration.

SUMMARY OF THE INVENTION

The present invention has been made in view of the above mentioned problems involved with the conventional glucose-measuring sensors, and an object of the invention is to provide a glucose strip sensor including a sample introducing port arranged at a front surface of the sensor, and discharge ports respectively arranged at opposite side surfaces of the sensor, thereby being capable of achieving convenience in handling the sensor, while additionally including a checking electrode adapted, alone or along with a counter electrode, to determine whether or not a sufficient amount of blood sample is introduced in the sensor, thereby being capable of achieving an accurate glucose measurement, and to provide a glucose measurement method using the glucose strip sensor.

In accordance with one aspect, the present invention provides a glucose strip sensor comprising a non-conductive substrate, a lead section formed on the substrate, the lead section including leads and lead terminals, an electrode section formed on the lead section and provided at an upper surface thereof with a reaction layer, the electrode section including an operating electrode, a counter electrode, and a checking electrode, a resin plate adapted to define, over the electrode section, a space for receiving a blood sample, a cover formed on the resin plate, a sample introducing port adapted to introduce the blood sample into the space, and discharge ports adapted to vent air from the space, wherein:

the electrode section further includes at least one checking electrode adapted to check whether or not the blood sample is completely introduced in the space; and the lead section further includes a lead and a lead terminal for the checking electrode.

The sample introducing port may be arranged at a front surface of the sensor, and the discharge ports are arranged at opposite side surfaces of the sensor, respectively.

In accordance with another aspect, the present invention provides a glucose measurement method comprising the steps of checking whether or not an electrical connection is established between the counter electrode and the checking electrode included in the glucose strip sensor or between the checking electrode and another checking electrode, thereby determining whether or not a blood sample is introduced in the space in a sufficient amount; and if it is determined the blood sample is introduced in the space in a sufficient amount, then measuring a glucose concentration of the blood sample in accordance with a well-known method.

BRIEF DESCRIPTION OF THE DRAWINGS

The above and other objects, features and other advantages of the present invention will be more clearly understood from the following detailed description taken in conjunction with the drawings, in which.

DESCRIPTION OF THE PREFERRED EMBODIMENTS

Figure 3:
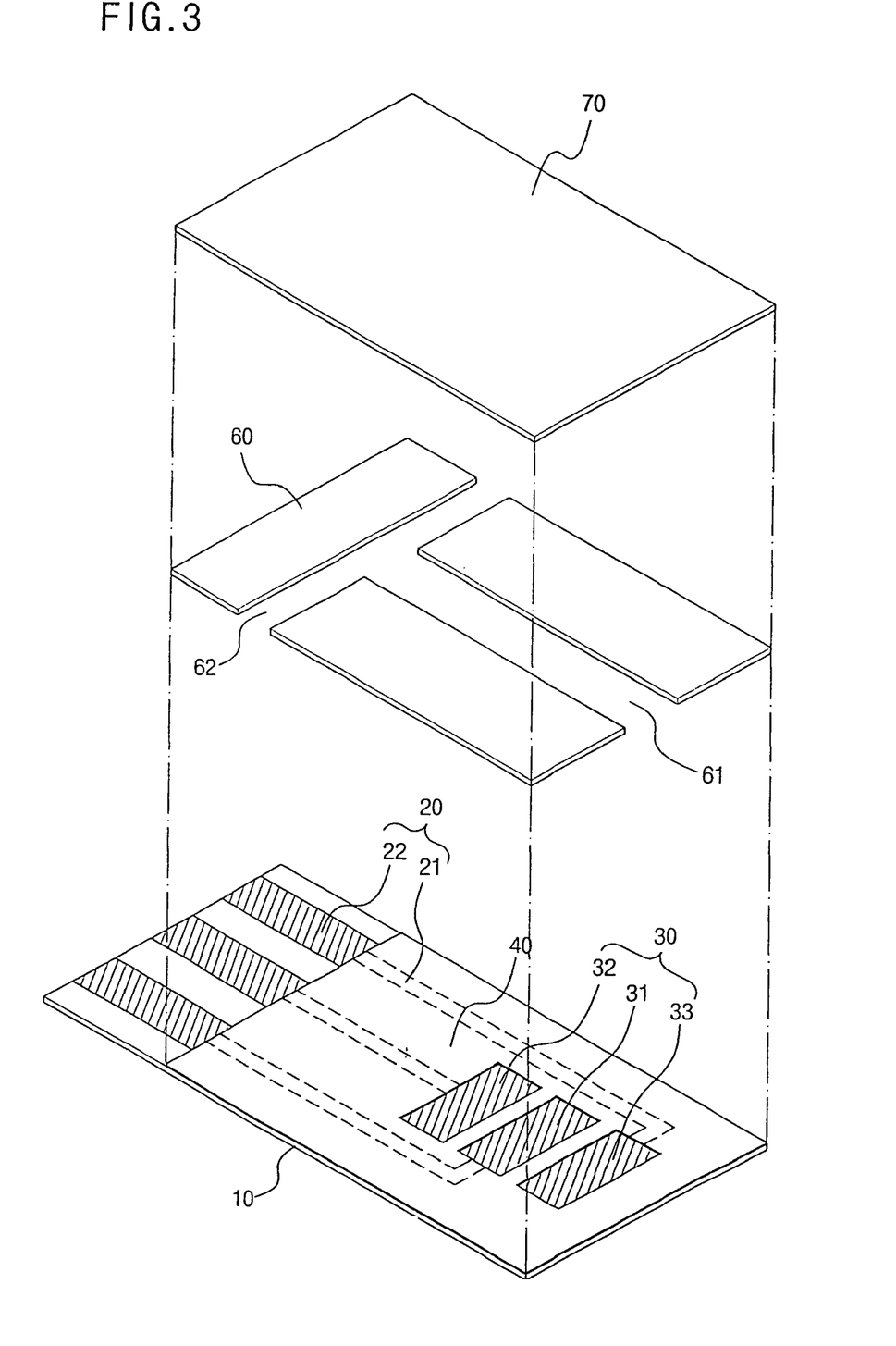
FIG. 3 is an exploded perspective view illustrating a glucose strip sensor according to an embodiment of the present invention.
Figure 4:
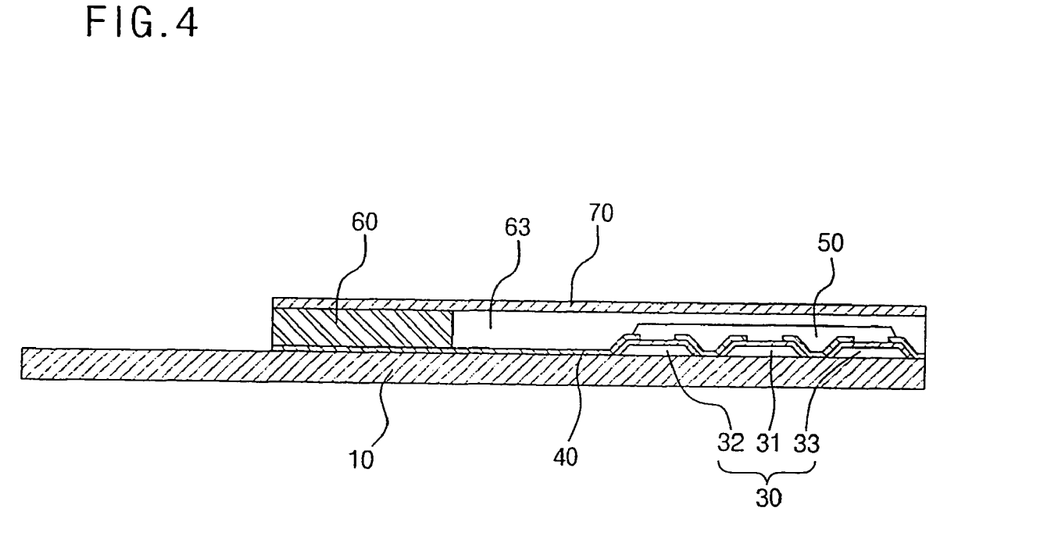
FIG. 4 is a sectional view of the glucose strip sensor illustrated in FIG. 3.
Figure 5:
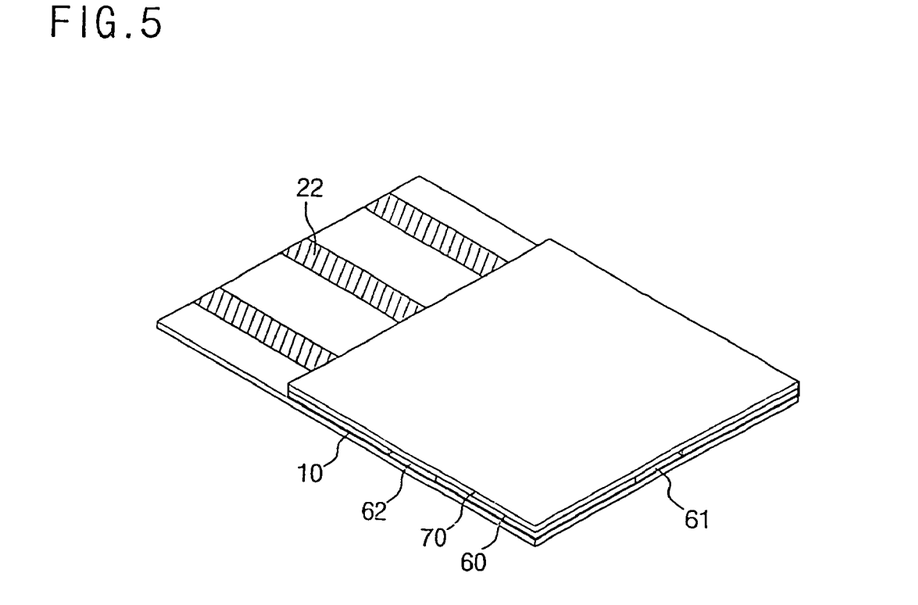
FIG. 5 is an assembled perspective view of the glucose strip sensor illustrated in FIG. 3.

FIG. 3 is an exploded perspective view illustrating a glucose strip sensor according to an embodiment of the present invention. FIG. 4 is a sectional view of the glucose strip sensor illustrated in FIG. 3. FIG. 5 is an assembled perspective view of the glucose strip sensor illustrated in FIG. 3.

As shown in FIGS. 3 to 5, the glucose strip sensor includes a non-conductive substrate 10, a lead section 20 formed on the substrate 10 by a silver ink or an ink mixture of silver and silver chloride, and an electrode section 30 formed on the lead section 20. The lead section 20 includes leads 21 and lead terminals 22, whereas the electrode section 30 includes an operating electrode 31, a counter electrode 32, and a checking electrode 33. The glucose strip sensor also includes an insulating layer 40 coated on the lead and electrode sections 20 and 30 while allowing the lead and electrode sections 20 and 30 to be partially exposed, a reaction layer 50 formed on the exposed portion of the electrode section 30, a resin plate 60 formed on the structure obtained after the formation of the reaction layer 50, and a cover 70 formed on the resin plate 60. The resin plate 60 defines a space 63, a sample introducing port 61, and discharge ports 62. The sample introducing port 61 is arranged at the front surface of the glucose strip sensor, whereas the discharge ports 62 are arranged at opposite side surfaces of the glucose strip sensor, respectively.

The glucose strip sensor of the present invention is characterized in that it includes, in addition to the operating electrode 31 and counter electrode 32, the checking electrode 33 for checking whether or not a sample is completely introduced in the sensor. The glucose strip sensor of the present invention is also characterized in that the sample introducing port 61 is arranged at the front surface of the glucose strip sensor, whereas the discharge ports 62 are arranged at opposite side surfaces of the glucose strip sensor, respectively.

Now, the fabrication of the glucose strip sensor having the above described structure will be described in detail.

First, the substrate 10 is prepared. For the substrate 10, a polymer substrate may be used which is made of a non-conductive material such as polyethylene terephthalate, polyvinyl chloride resin, or polycarbonate resin. The substrate 10 is preferably made of polyethylene terephthalate.

The formation of the lead section 20 on the substrate 10 is then performed. As mentioned above, the lead section 20 includes the leads 21 and lead terminals 22. The lead section 20 may be formed using a well-known screen printing method. In accordance with the present invention, the lead section 20 is formed by screen-printing a silver ink or an ink mixture of silver and silver chloride on the substrate 10.

Figure 6:
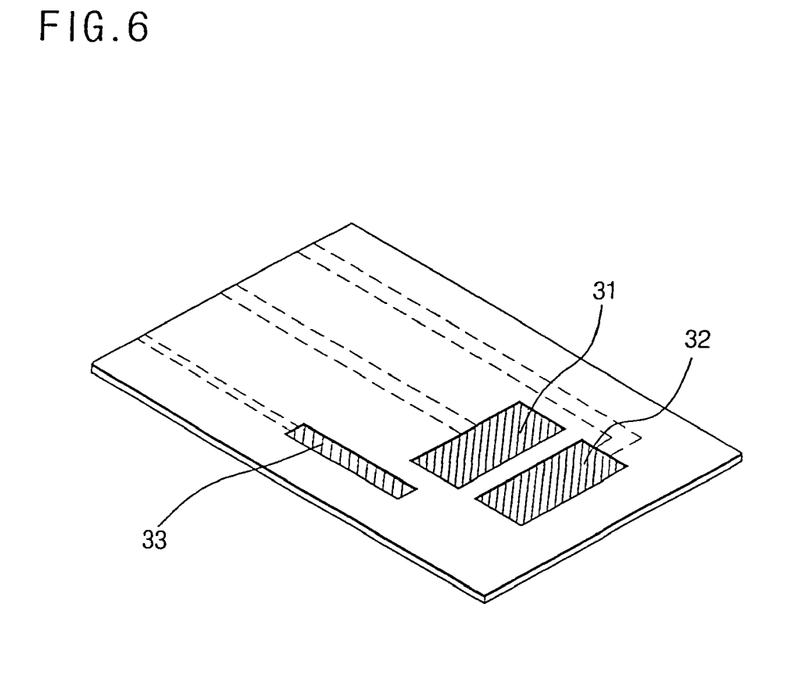
FIG. 6 is a perspective view illustrating an electrode arrangement in the glucose strip sensor according to the present invention.

After formation of the lead section 20, the electrode section 30 is formed on the lead section 20. In accordance with the present invention, the electrode section 30 includes the checking electrode 33 in addition to the operating electrode 31 and counter electrode 32. Although one checking electrode 33 is illustrated, the electrode section 30 may include two or more checking electrodes. Where the checking electrode 33 is arranged as shown in FIG. 6, it is checked whether or not the checking electrode 33 is electrically connected with the counter electrode 32. Based on the result of the checking, it is possible to determine whether or not the blood sample is sufficiently filled in the sensor. Accordingly, the glucose concentration in the blood sample can be accurately measured.

Under the condition in which the checking electrode 33a determines that a sufficient amount of blood sample is introduced in the sensor, the checking electrode 33 can perform the same function as the counter electrode 32 because the checking electrode 33 is electrically connected with the counter electrode 32. In this case, an increased counter electrode area is obtained. By virtue of such an increased counter electrode area, it is possible to obtain a glucose measuring signal with an increased sensitivity when the amount of current flowing between the operating electrode and the counter electrode is measured. The operating electrode 31 and counter electrode 32, which form the electrode section 30, may be formed using a well-known method. The formation of the checking electrode 33 may also be achieved in the same manner as the formation of the counter electrode 32. As mentioned above, the electrode section 30 is preferably formed in accordance with a screen printing method using a conductive carbon ink.

On the upper surface of the resulting structure obtained after formation of the electrode section 30, an insulating material is screen-printed to form the insulating layer 40 for insulating the lead section 20 while partially exposing the electrode section 30. For the insulating material, a non-conductive screen printing ink or an insulating ink may be used. In accordance with the present invention, the insulating screen printing ink is preferably used. Thereafter, the formation of the reaction layer 50 is carried out in such a fashion that the reaction layer 50 covers the exposed portion of the electrode section 30. The reaction layer 50 is made of a material including hydrogel and glucose oxidase (GOD) as major components thereof. In detail, the formation of the reaction layer 50 is achieved by preparing a solution obtained by respectively mixing hydrogel, GOD and a stabilizer in a liquid buffer at desired rates, dispensing the solution onto the surface of the electrode section 30, and then drying the dispensed solution in an incubator.

On the resulting structure obtained after formation of the reaction layer 50 including hydrogel and GOD as major components thereof, a resin plate 60 is arranged to define a space 63. Also, the resin plate 60 defines the sample introducing port 61 at the front surface of the sensor and the discharge ports 62 at respective side surfaces of the sensor. Since the sample introducing port 61 and discharge ports 62 are formed at the front and side surfaces of the sensor, respectively, it is possible to conveniently handle the sensor, as compared to the conventional sensor including a discharge port formed at the upper surface of the sensor.

The cover 70 is finally arranged on the resin plate 60 using a well-known method. Thus, the fabrication of the glucose strip sensor according to the present invention is completed.

Since the glucose strip sensor having the above mentioned structure includes the checking sensor 33, it is possible to check whether or not the checking sensor 33 is electrically connected with the counter electrode 32, thereby determining whether or not the sensor is filled with a sufficient amount of blood sample. Accordingly, there is an advantage in that the measured glucose concentration has an increased accuracy. In addition, where the amount of current flowing between the counter electrode 32 and the checking electrode 33 is measured under the condition in which those electrodes are electrically connected using conduction means, there is an advantage in that a glucose measuring signal with an increased sensitivity can be obtained. Since the sample introducing port 61 and discharge ports 62 are formed at the front and side surfaces of the sensor, respectively, it is also possible to conveniently handle the sensor.

In the case of FIG. 3, the arrangement of the operating electrode 31, counter electrode 32, and checking electrode 33 is made in such a fashion that the counter electrode 32 and checking electrode 33 are arranged at front and rear sides of the operating electrode 31, respectively. However, other arrangements may be implemented.

For example, the counter electrode 32 may be arranged near the sample introducing port 61, and the checking electrode 33 may be arranged near one of the discharge ports 62, as shown in FIG. 6. In this case, the checking electrode 33 is electrically connected with the counter electrode 32 under the condition in which the space 63 of the sensor is completely filled with a blood sample. Accordingly, it is possible to accurately check whether or not the space of the sensor is completely filled with a blood sample even when the space has an increased volume.

Figure 7:
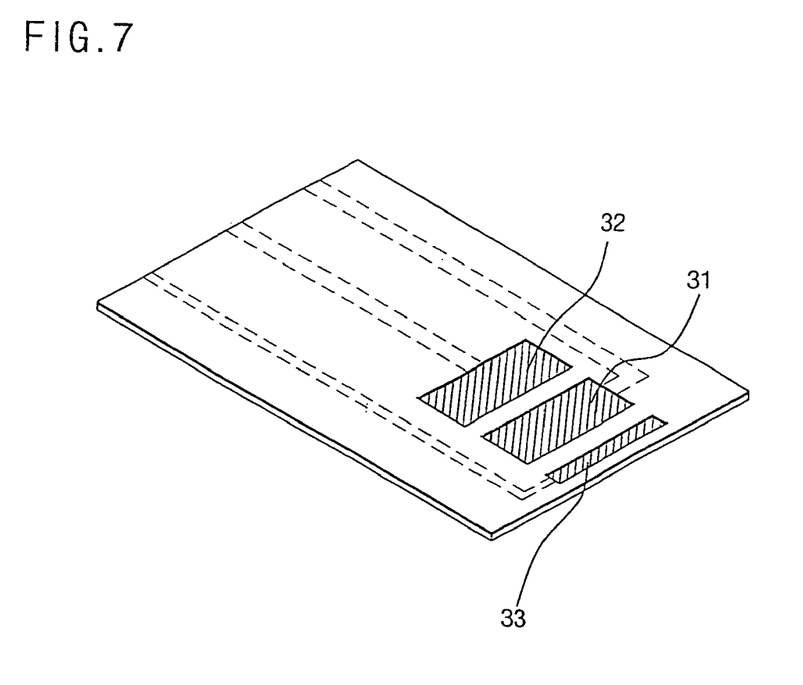
FIG. 7 is a perspective view illustrating another electrode arrangement in the glucose strip sensor according to the present invention.

It is also possible to arrange the checking electrode 33 near the sample introducing port 61 while arranging the counter electrode 32 in rear of the operating electrode 31, as shown in FIG. 7.

Using the checking electrode having the arrangement illustrated in FIG. 6 or 7, it is possible to accurately determine whether or not a sufficient amount of blood sample is introduced in the sensor. Accordingly, measurement errors can be reduced.

The operation of the glucose strip sensor having the above described structure according to the present invention will now be described in detail. When a blood sample comes into contact with the sample introducing port 61 of the sensor, it is introduced into the space 63 of the sensor by virtue of capillary phenomenon, so that it fills the space 63. Simultaneously, air existing in the space 63 is vented from the space 63 through the discharge ports 62 respectively formed at opposite side surfaces of the sensor. Thereafter, it is checked, prior to a desired measurement of glucose concentration, whether or not a sufficient amount of blood sample is introduced in the space 63. That is, it is checked whether or not an electrical connection is established between the counter electrode 32 and the checking electrode 33.

The blood sample filled in the space 63 of the sensor is impregnated into the reaction layer 50. The glucose of the impregnated blood sample enzymatically reacts with the GOD contained in the reaction layer 50, so that it is oxidized. Simultaneously, the GOD is reduced. The reduced GOD is then oxidized as it reacts with the electron acceptor contained in the reaction layer 50, whereas the oxidized GOD reacts with the glucose not yet oxidized. The reduced electron acceptor migrates to the surface of the operating electrode 31, to which voltage of about 0.6 V is applied, and donates electrons at that surface. Simultaneously, the electron acceptor is reoxidized so that it takes part again in the above reaction. The current generated during the oxidation of the electron acceptor is proportional to the concentration of glucose in the blood sample. Accordingly, the glucose concentration in the blood sample can be quantitatively derived by measuring the amount of current flowing between the operating electrode 31 and the counter electrode 32.

An experiment was made in order to identify correlations established between the glucose concentration measured by the glucose strip sensor according to the present invention and the glucose concentration measured by an automatic glucose analyzer. The experiment was carried out as follows.

Figure 8:
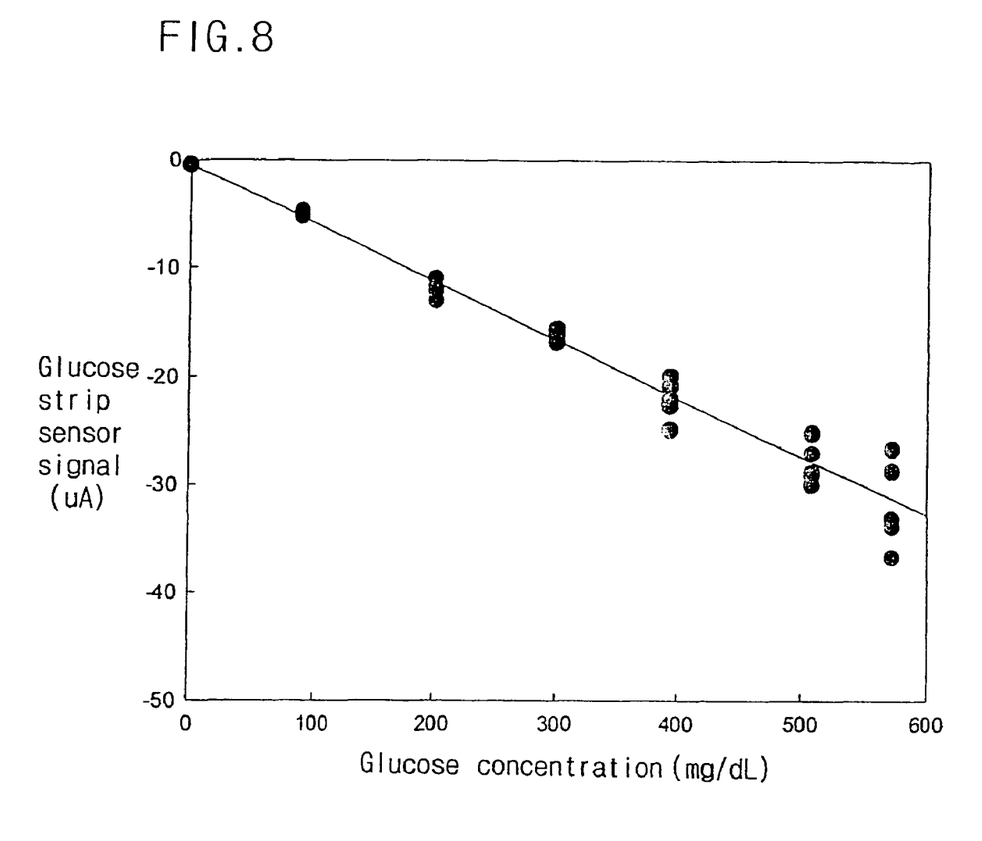
FIG. 8 is a graph depicting the correlation of a signal generated by the glucose strip sensor according to the present invention with respect to glucose concentration.

First, a blood sample was prepared by dissolving a desired amount of glucose in a buffer solution. Thereafter, the concentration of glucose in the blood sample was measured using an automatic glucose analyzer, which is the Model YSI 2300 STAT PLUS manufactured by YSI Inc. The signal intensity corresponding to the measured glucose concentration was then measured by the glucose strip sensor according to the present invention. The correlation between the measured glucose concentration and the measured signal intensity is depicted in FIG. 8. The measurement was repeated 6 times for each glucose concentration.

Referring to FIG. 8, it can be seen that the correlation between the measured glucose concentration and the measured signal intensity is well established in a clinically important glucose concentration range, that is, a glucose concentration range of 50 to 600 mg/dL.

As apparent from the above description, the present invention provides a glucose strip sensor in which a checking electrode is additionally provided at an electrode section including an operating electrode and a counter electrode. The checking electrode serves to check whether or not it is electrically connected with the counter electrode, upon measuring the concentration of glucose in a blood sample introduced in the sensor. Based on the result of the checking, it is possible to determine whether or not a sufficient amount of blood sample is filled in the sensor. Accordingly, the measurement of glucose concentration can be accurately achieved. Moreover, where the amount of current flowing between the counter electrode and the checking electrode is measured under the condition in which those electrodes are electrically connected using conduction means, there is an advantage in that a glucose measuring signal with an increased sensitivity can be obtained.

In accordance with the present invention, the glucose strip sensor also includes a sample introducing port arranged at the front surface of the sensor, and discharge ports arranged at respective side surfaces of the sensor. Accordingly, it is also possible to conveniently handle the sensor.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A glucose strip sensor comprising:
   a non-conductive substrate;
   an electrode section formed on the substrate, the electrode section including an operating electrode and a counter electrode respectively electrically connected to lead terminals by leads;
   a reaction layer formed over the electrode section and being adapted to react with a blood sample;
   a resin plate adapted to define, over the electrode section, a sample receiving space for receiving the blood sample;
   a cover arranged on the resin plate;
   a sample introducing port arranged on a front end portion of the resin plate, the sample introducing port being adapted to introduce the blood sample into the sample receiving space by virtue of capillary phenomenon; and
   discharge ports arranged on opposite sides of the glucose strip sensor and being defined by the resin plate, the discharge ports being adapted to vent air from the sample receiving space,
   wherein the electrode section further comprises at least one checking electrode arranged near one of the discharge ports, the at least one checking electrode being adapted to check whether or not the blood sample is completely introduced in the sample receiving space.

2. The sensor of claim 1, wherein the at least one checking electrode is electrically connected with the counter electrode under the condition in which the sample receiving space is completely filled with the blood sample, whereby the checking electrode functions to increase a area of the counter electrode, whereby a glucose measuring signal with an increased sensitivity is obtained.

3. The sensor of claim 1, wherein the glucose strip sensor comprises a lower surface defined by the substrate, a upper surface defined by the cover, a front edge and side edges defined by the cover, the substrate, and the resin plate.

4. The sensor of claim 1, wherein the sample introducing port is arranged on a front side edge of the glucose strip sensor.

5. The sensor of claim 1, wherein the discharge ports are arranged on opposite side edges of the glucose strip sensor.

6. The sensor of claim 1, wherein the sample introducing port is arranged on a front side edge of the glucose strip sensor and is defined by the cover, the resin plate, and the substrate.

7. The sensor of claim 1, wherein the discharge ports are arranged on opposite side edges of the glucose strip sensor and is defined by the cover, the resin plate, and the substrate.

8. The sensor of claim 1, wherein the non-conductive substrate comprises a non-conductive polymer material comprising at least one of polyvinyl chloride resin and polycarbonate resin.

9. The sensor of claim 1, wherein the leads are formed by screen printing.

10. The sensor of claim 1, wherein the reaction layer comprises at least hydrogel and glucose oxidase.

11. A glucose measurement method comprising:
    introducing a blood sample into the glucose strip sensor comprising a non-conductive substrate, an electrode section formed on the substrate, the electrode section including an operating electrode and a counter electrode respectively electrically connected to lead terminals by leads, a reaction layer formed over the electrode section and being adapted to react with a blood sample, a resin plate adapted to define, over the electrode section, a sample receiving space for receiving the blood sample, a cover arranged on the resin plate, a sample introducing port arranged on a front end portion of the resin plate, the sample introducing port being adapted to introduce the blood sample into the sample receiving space by virtue of capillary phenomenon, and discharge ports arranged on opposite sides of the glucose strip sensor and being defined by the resin plate, the discharge ports being adapted to vent air from the sample receiving space, wherein the electrode section further comprises at least one checking electrode arranged near one of the discharge ports, the at least one checking electrode being adapted to check whether or not the blood sample is completely introduced in the sample receiving space;

checking whether or not an electrical connection is established between the counter electrode and the checking electrode in order to determine whether or not the blood sample is introduced in the sample receiving space in a sufficient amount; and if it is determined the blood sample is introduced in the sample receiving space in a sufficient amount, having the counter electrode also function as a counter electrode thereby increasing the counter electrode area, whereby a glucose measuring signal with an increased sensitivity is obtained; and measuring a glucose concentration of the blood sample electrochemically.

* * * * *